(12) United States Patent
Stec et al.

(10) Patent No.: US 11,742,060 B2
(45) Date of Patent: Aug. 29, 2023

(54) METHODS, SYSTEMS AND APPARATUS FOR GENERATING CHEMICAL DATA SEQUENCES USING NEURAL NETWORKS FOR DE NOVO CHEMICAL FORMULATIONS

(71) Applicant: Potion AI, Inc., Brooklyn, NY (US)

(72) Inventors: Alexander Anthony Stec, Hinsdale, IL (US); Yahya Muhammad Syed, Brooklyn, NY (US); Qijian He, New York, NY (US)

(73) Assignee: Potion AI, Inc., Brooklyn, NY (US)

( * ) Notice: Subject to any disclaimer, the term of this patent is extended or adjusted under 35 U.S.C. 154(b) by 0 days.

(21) Appl. No.: 17/815,454

(22) Filed: Jul. 27, 2022

(65) Prior Publication Data

US 2022/0359043 A1 Nov. 10, 2022

Related U.S. Application Data

(63) Continuation of application No. PCT/US2021/015108, filed on Jan. 26, 2021.
(Continued)

(51) Int. Cl.
*G16C 20/10* (2019.01)
*G16C 20/70* (2019.01)
(Continued)

(52) U.S. Cl.
CPC ........... *G16C 20/10* (2019.02); *G06F 18/217* (2023.01); *G06N 3/044* (2023.01); *G16C 20/70* (2019.02)

(58) Field of Classification Search
CPC ........ G16C 20/10; G06F 18/217; G06N 3/044
See application file for complete search history.

(56) References Cited

U.S. PATENT DOCUMENTS

| 6,421,612 B1 * | 7/2002 | Agrafiotis ............... G06F 18/40 702/19 |
| 10,915,818 B1 | 2/2021 | Patel et al. |

(Continued)

FOREIGN PATENT DOCUMENTS

WO WO-2017074455 A1 5/2017

OTHER PUBLICATIONS

International Preliminary Examination Report for Application No. PCT/US2021/015108, dated Aug. 11, 2022, 7 pages.
(Continued)

*Primary Examiner* — Bryan Bui
(74) *Attorney, Agent, or Firm* — Cooley LLP

(57) ABSTRACT

In some embodiments, a method includes receiving a set of target attributes associated with a chemical product formulation and a set of priority values of the plurality of target attributes. The method includes determining, based on (1) a first neural network, (2) the set of target attributes and (3) the set of priority values, a set of sample formulations. The method includes determining a set of scores based on the set of sample formulations. The method includes selecting, based on the set of scores and the set of target attributes, a sample formulation from the set of sample formulations having a score greater than remaining scores from the set of scores. The method includes determining an origin associated with the sample formulation. When the origin is included in a pre-determined group, the method includes generating a report including the sample formulation as the chemical product formulation.

23 Claims, 6 Drawing Sheets

Related U.S. Application Data

(60) Provisional application No. 62/966,409, filed on Jan. 27, 2020.

(51) Int. Cl.
  *G06F 18/21* (2023.01)
  *G06N 3/044* (2023.01)

(56) References Cited

U.S. PATENT DOCUMENTS

| | | |
|---|---|---|
| 2003/0014191 A1 | 1/2003 | Agrafiotis et al. |
| 2008/0010027 A1 | 1/2008 | Alman |
| 2020/0327377 A1 | 10/2020 | Jaganathan et al. |

OTHER PUBLICATIONS

International Search Report and Written Opinion for Application No. PCT/US2021/015108, dated Apr. 8, 2021, 7 pages.

\* cited by examiner

METHODS, SYSTEMS AND APPARATUS FOR GENERATING CHEMICAL DATA SEQUENCES USING NEURAL NETWORKS FOR DE NOVO CHEMICAL FORMULATIONS

CROSS-REFERENCE TO RELATED APPLICATIONS

This application is a continuation of International Application No. PCT/US2021/015108, filed Jan. 26, 2021, which claims priority to and benefit of U.S. Provisional Application No. 62/966,409, titled "Methods, Systems and Apparatus for Generating Chemical Data Sequences Using Neural Networks for De Novo Chemical Formulations," filed Jan. 27, 2020, the entire disclosure of which is incorporated herein by reference in its entirety.

BACKGROUND

Some embodiments described herein relate generally to methods, systems, and apparatus for artificial intelligence. In particular, but not by way of limitation, some embodiments described herein relate to methods, systems, and apparatus for generating chemical data sequences using neural networks for de novo chemical formulations.

Chemical formulations are typically created, designed and/or formulated using empirical methodologies or basic modeling methodologies, oftentimes by product formulators or, in the case of beauty products, cosmetic chemists. Such methodologies are time-consuming, expensive, imprecise, and generally do not result in optimum designs/formulations. When creating new chemical formulations with a specific target attribute(s) (such as selected efficacy or physical properties), formulators typically rely on existing formulations to serve as formulatory bases, as opposed to creating de novo formulations that are singularly optimized for the targeted objectives. This approach yields formulations that are compromised compared to de novo formulations that are designed from the ground up to meet a targeted objective. Additionally, formulations designed in this manner often face stability issues, with a high percentage of products ultimately failing in the testing stage due to unanticipated problems such as product separation. Finally, these methodologies are not optimized for a subset of other issues that have eluded formulators for ages, including 1) interactions of various constituent chemicals with each other in a formulation, and 2) interactions of formulations with external subjects (e.g., human skin).

Thus, a need exists for a better methodology that obviates the shortcomings of such methods.

SUMMARY

This specification describes how an apparatus implemented as computer programs on one or more computers in one or more locations takes desired formulation attributes as input and generates sequences of chemical data constituting chemical formulations. For example, the sequence of chemical data can represent a skincare product formulation such as a facial moisturizer.

The apparatus includes a signal encoding subsystem implemented by one or more computers, termed the signal encoder, configured to receive as input one or more target attributes and to encode these attributes as a signal for communication to other subsystems within the apparatus. The apparatus includes a subsystem implemented by one or more computers, termed the generator, configured to generate chemical data sequences that the apparatus then transforms into corresponding chemical formulations.

In one innovative aspect the generator includes a neural network subsystem implemented by one or more computers, termed the generator sequence subsystem, that is configured to take as input (i) a chemical data sequence (ii) in some embodiments a signal comprised of desired formulation attributes and is configured to generate an output sequence of chemical data that composes a chemical formulation. The generator sequence subsystem may comprise partly or fully of a recurrent neural network comprising one or more signal processing layers and one or more output layers. The generator sequence subsystem may further be configured to process the current sequence of chemical data to generate an alternative representation for the current time step. This alternative representation may thus comprise a numeric representation, i.e. an ordered collection of numeric values, in which the current sequence of chemical data has been encoded by the generator sequence subsystem. The output layers may be configured, for all time steps, to receive and process the alternative representation for the time step to generate an output of chemical data for that time step. In some embodiments, the generator subsystem also includes a subsystem, termed the template subsystem, that acts in tandem with the generator sequence subsystem and may modify the chemical data sequence produced by the generator sequence subsystem between time steps.

The apparatus in some embodiments also includes a neural network subsystem implemented by one or more computers, termed the predictor, that is configured to receive as input a sequence of chemical data representing a chemical formulation. The predictor may comprise partly or fully of a recurrent neural subnetwork that may be augmented with an external memory. The subnetwork may comprise of one or more signal processing layers and one or more output layers, where the output layers are configured to predict the extent to which the given chemical formulation represented by the input chemical data sequence manifests target attributes corresponding to that particular output layer.

The apparatus in some embodiments also includes a neural network subsystem implemented by one or more computers, termed the discriminator, that is configured to receive input of the same format as the predictor. In some embodiments the discriminator may comprise partly or fully of a recurrent neural subnetwork that may be augmented with an external memory and in other embodiments the discriminator may comprise partly or fully of a convolutional neural subnetwork. The subnetwork may comprise one or more signal processing layers and an output layer, where the output layer is configured to predict values associated with assigning which of a multitude of sets the chemical formulation represented by the input chemical data sequence originates from, e.g., having been produced by the generator versus being a member of a set of products currently in the market.

The apparatus in some embodiments also includes a reinforcement learning subsystem implemented by one or more computers, termed the tuner, that is configured to receive as input (i) a signal comprised of desired formulation attributes, (ii) a generator sequence subsystem and one or more of the following, (iii) the predictor subsystem and (iv) the discriminator subsystem. The tuner is configured to modify the neural network weights of the generator sequence subsystem with the aim of modifying the generator sequence subsystem (in some implementations, generate a modified neural network to increase the scores) such that the output chemical data sequences are more likely to represent chemical formulations exhibiting the desired attributes.

The apparatus also includes a subsystem, termed the formulation selector, for transforming chemical data sequences generated by the generator into chemical formulations, and then for selecting a subset of these formulations to take as output of the apparatus. In some embodiments, the formulation selector subsystem also receives as input the output from one or both of the predictor and discriminator subsystems corresponding to the chemical data sequences it receives. The formulation selector may be configured to optimize the selection of formulations represented by the chemical data sequences that score highly on scores corresponding to the desired attributes.

The disclosure may be expressed as a computer-implemented method, or as a computer system, or as a computer program product (such as one or more computer storage media) storing program instructions which cause one or more computers to perform the method, to implement the computer system. The details of one or more embodiments of the subject matter described in this specification are set forth in the accompanying drawings and the description below. Other features, aspects, and advantages of the subject matter will become apparent from the description, the drawings, and the claims.

In some embodiments, a method includes receiving a set of target attributes associated with a chemical product formulation and a set of priority values of the plurality of target attributes. The method includes determining, based on (1) a first neural network, (2) the set of target attributes and (3) the set of priority values, a set of sample formulations. Each sample formulation from the set of sample formulations includes a set of ingredients. The method includes determining a set of scores based on the set of sample formulations. Each score from the set of scores is associated with a sample formulation from the set of sample formulations. The method includes selecting, based on the set of scores and the set of target attributes, a sample formulation from the set of sample formulations having a score greater than remaining scores from the set of scores. The method includes determining an origin associated with the sample formulation. When the origin is included in a pre-determined group, the method includes generating a report including the sample formulation as the chemical product formulation.

In some embodiments, a non-transitory processor-readable medium stores code representing instructions to be executed by a processor. The code comprises code to cause the processor to receive a set of target attributes for a chemical formulation. The code comprises code to cause the processor to encode the set of target attributes to generate a signal. The code comprises code to cause the processor to determine, using a first neural network with the signal as a first input, (1) a chemical data sequence including a set of ingredients and (2) a set of characteristic values. Each ingredient from the set of ingredients is associated with a characteristic value from the set of characteristic values. The code comprises code to cause the processor to determine, using a second neural network and with the chemical data sequence and the set of characteristic values as a second input, a set of scores of the set of ingredients and associated with the set of target attributes. The code comprises code to cause the processor to modify a set of weights associated with the first neural network to increase the set of scores and generate a modified neural network. The code comprises code to cause the processor to determine, based on the modified neural network, a modified chemical data sequence including a modified set of ingredients. The code comprises code to cause the processor to generate a report including the chemical formulation having the modified chemical data sequence associated with the set of target attributes.

In some embodiments, an apparatus comprises a processor and a memory operatively coupled to the processor. The memory stores code representing instructions to be executed by a processor. The code comprises code to cause the processor to receive a set of target attributes associated with a chemical product formulation. The code comprises code to cause the processor to determine, based on a first neural network, a first set of sample formulations associated with the set of target attributes. Each sample formulation from the first set of sample formulations includes a set of ingredients. The code comprises code to cause the processor to determine a first set of scores. Each score from the first set of scores is associated with a sample formulation from the first set of sample formulations. The code comprises code to cause the processor to select, based on the first set of scores and the set of target attributes, a first sample formulation from the first set of sample formulations having a score greater than remaining scores from the first set of scores. The code comprises code to cause the processor to determine, based on the first neural network and the first sample formulation, a second set of sample formulations. The code comprises code to cause the processor to determine a second set of scores. Each score from the second set of scores is associated with a sample formulation from the second set of sample formulations. The code comprises code to cause the processor to select, based on the second set of scores and the set of target attributes, a second sample formulation from the second set of sample formulations having a score greater than remaining scores from the second set of scores. The code comprises code to cause the processor to determine an origin associated with the second sample formulation. When the origin is included in a pre-determined group, the code comprises code to cause the processor to generate a report including the second sample formulation as the chemical product formulation.

DETAILED DESCRIPTION

The systems, methods, and devices will now be described, according to one or more embodiments. The example embodiments are presented in this disclosure for illustrative purposes, and not intended to be restrictive or limiting on the scope of the disclosure but instead are more broadly applicable to other suitable systems, methods, and devices.

Embodiments described herein provide techniques for the formulation of chemical products that exhibit one or more target attributes. Here, a formulation is a mixture of chemicals that is designed to produce a product with certain target attributes. In some embodiments, a formulation is provided as a set of ingredients composing the product. This set of ingredients may be ordered in a list according to descending ingredient concentration by percentage weight in the product. In some embodiments, a formulation is a set or list of ingredients along with one or more values associated with each ingredient. These values associated with each ingredient may provide additional instruction in the formulation of the product with respect to using that particular ingredient. By way of example, one numerical value can correspond to the respective ingredient's concentration by percentage weight in the final product. As another example, one value can indicate at what mixing stage each ingredient is incorporated into the product, i.e., the order and manner in which the ingredients are mixed together.

This specification uses the term "target attribute(s)" in connection with products given by chemical formulations as described above. Here, an attribute is generally a quality or feature that is an inherent part of the product and specifying that an attribute is a target generally means that it is desirable for a product to exhibit that particular attribute. As an example, an attribute of a product produced by a chemical formulation may be the class of the product, e.g. skin care v. hair care, and may be a physical attribute of the product, such as the product's viscosity or pH level. One or more embodiments described herein are designed to output product formulations that are optimized and selected to exhibit one or more target attributes. This optimization will be more fully described below when the subsystem responsible for outputting formulations is detailed.

Figure 1:
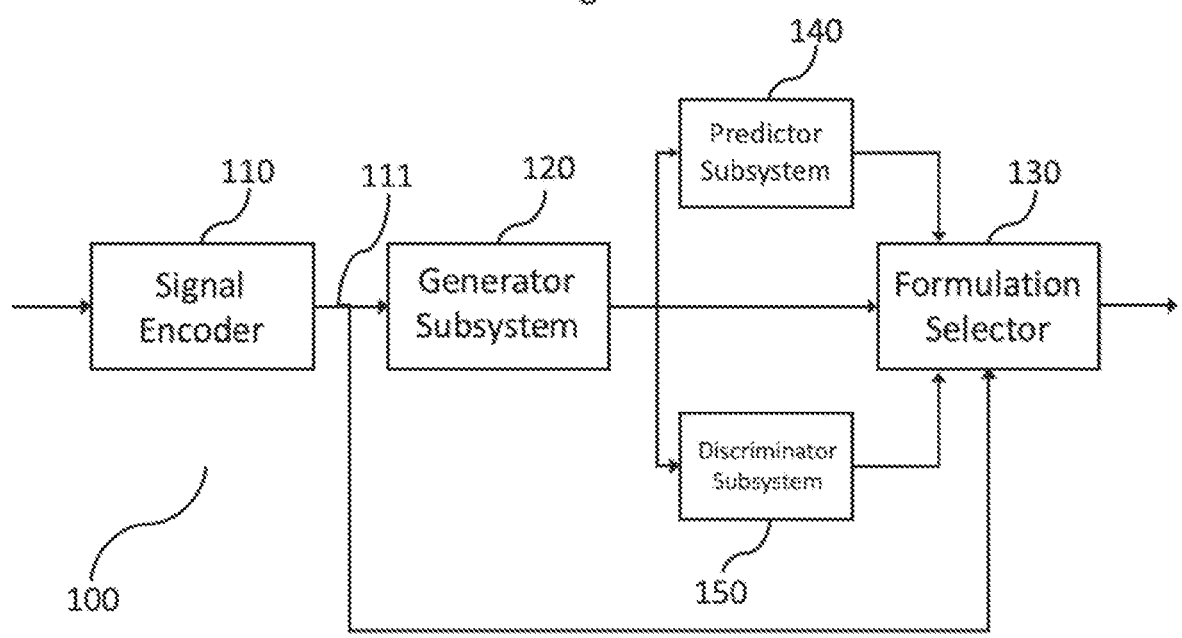
FIG. 1 illustrates an apparatus for the chemical formulation of products with desired formulation attributes, according to an embodiment.

FIG. 1 illustrates a chemical product formulation apparatus 100 that takes as input desired attributes and communicates one or more target attribute signals to formulate one or more products given by chemical product formulations. The chemical product formulation can include a set of ingredients. The chemical product formulation can be, for example, a personal care (e.g., skin care) product formulation. The chemical product formulation apparatus 100 comprises a signal encoder 110, a generator subsystem 120, and a formulation selector 130. As shown in FIG. 1, signal encoder 110 is operatively coupled to and in communication with generator subsystem 120 and formulation selector 130; generator subsystem 120 is operatively coupled to and in communication with predictor subsystem 140, discriminator subsystem 150 and formulation selector 130; predictor subsystem 140 and discrimination subsystem 150 are each operatively coupled to and in communication with formulation selector 130. The chemical product formulation apparatus 100 includes one or more processors (not shown in FIG. 1) and a memory (not shown in FIG. 1) operatively coupled to the one or more processors. The memory stores code representing instructions to be executed by the one or more processors. The code comprises code to cause the one or more processors to execute the signal encoder 110, the generator subsystem 120, the formulation selector 130, the predictor subsystem 140, and the discriminator subsystem 150.

Figure 2:
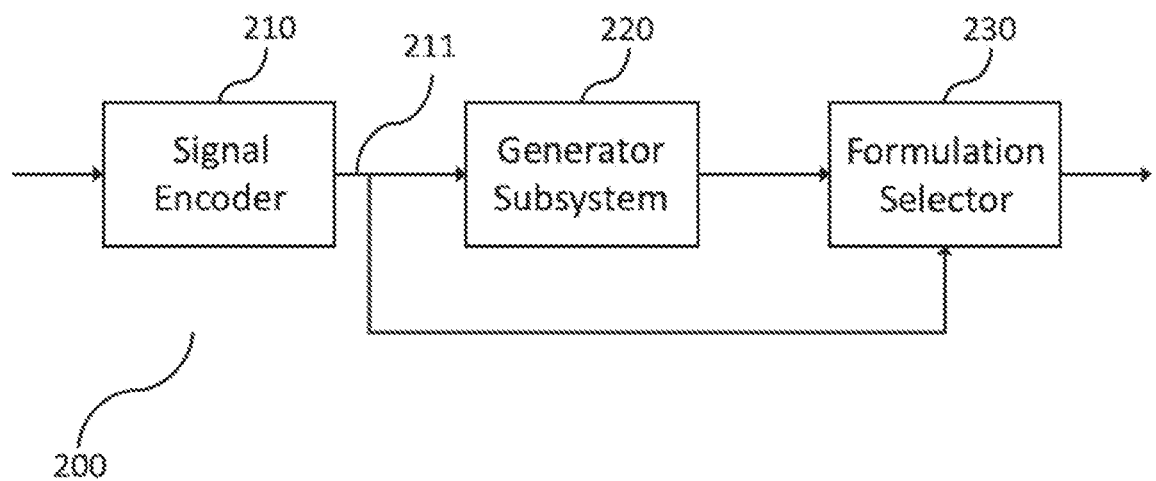
FIG. 2 illustrates another apparatus for the chemical formulation of products with desired formulation attributes, according to an embodiment.

In some embodiments the apparatus also optionally includes a predictor subsystem 140. In some embodiments the apparatus also optionally includes a discriminator subsystem 150. Note that FIG. 1 illustrates only one possible configuration of the chemical product formulation apparatus 100. In some other embodiments, one or both of the predictor subsystem 140 and the discriminator subsystem 150 may be excluded. FIG. 2 illustrates a possible configuration of a chemical product formulation apparatus 200 in which neither the predictor subsystem 140 nor the discriminator subsystem 150 are present. In this embodiment, the formulation selector 230 only receives the target attribute signal 211 and the generated chemical data sequences from the generator subsystem 220 as input. Similar in physical structure and functionalities to the chemical product formulation apparatus 100 in FIG. 1, the chemical product formulation apparatus 200 in FIG. 2 can also include one or more processors (not shown in FIG. 2) and a memory (not shown in FIG. 2) operatively coupled to the one or more processors. The memory stores code representing instructions to be executed by the one or more processors. The code comprises code to cause the one or more processors to execute the signal encoder 210, the generator subsystem 220, the formulation selector 230.

Returning to FIG. 1, the signal encoder 110 is configured to receive as input one or more target attributes and, in some implementations, encode these attributes as a signal for communication to the formulation selector 130. In some implementations, the generator subsystem 120 receives the one or more target attributes as input without the signal encoder 110 encoding these one or more target attributes. In some embodiments, the encoded target attribute signal 111 can be optionally communicated to the generator subsystem implementations 120 in addition to the formulation selector 130. In some implementations, the target attribute signal may partially or wholly include one-hot encodings or other representations that specify the class or category of products represented by formulations in the chemical product formulation apparatus 100 output. Continuous attributes may be mapped to a given set of discrete values (or a pre-determined set of discrete values) in the target attribute signal and therefore treated as class targets. In some embodiments, the attribute signal may partially or wholly include a vector of continuous values that specify numerical attributes that should appear in the products represented by formulations in the chemical product formulation apparatus 100 output, e.g. a physical attribute such as viscosity at a target value.

In some implementations, after the signal encoder 110 has encoded the target attribute signal 111, the processor at the chemical product formulation apparatus 100 (executing the generator subsystem 120 based on instructions stored in the memory of the chemical product formulation apparatus 100) can determine, using a neural network with the encoded signal as input, a chemical data sequence including a set of ingredients and a set of characteristic values. Each ingredient from the plurality of ingredients is associated with a characteristic value from the plurality of characteristic values. The generator subsystem 120 is configured to create chemical data sequences that will be communicated to the formulation selector 130. In some implementations, the generator subsystem 120 contains a neural network generator sequence subsystem. In some implementations, the target attribute signal 111 is used as input to the generator subsystem 120 (or a first neural network). In this case, the neural network generator sequence subsystem is conditioned to output chemical data sequences according to the target attribute signal 111 that is used as neural network input to the neural network generator sequence subsystem. In some implementations, the generator subsystem 120 contains a template subsystem in addition to the neural network generator sequence subsystem.

Figure 3:
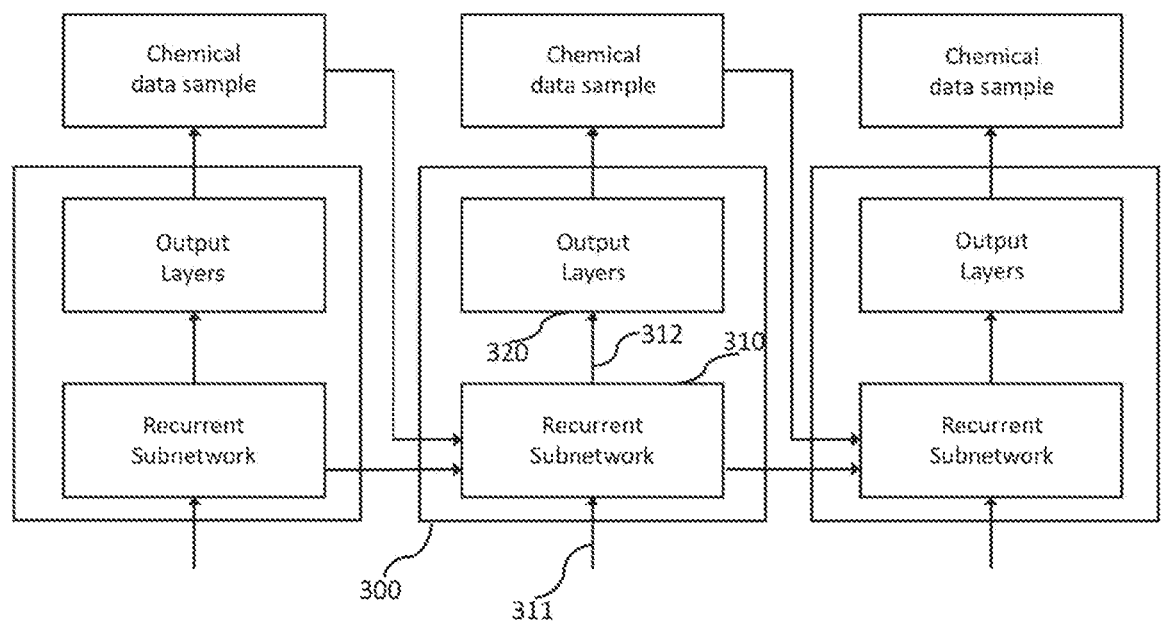
FIG. 3 illustrates a neural network generator sequence subsystem configured to perform the autoregressive generation of a chemical data sequence, according to an embodiment.

FIG. 3 illustrates an example neural network generator sequence subsystem 300. The example neural network generator sequence subsystem 300 can be stored in a memory and executed by a processor of a chemical product formulation apparatus (similar to the chemical product formulation apparatus 100 in FIG. 1 or the chemical product formulation apparatus 200 in FIG. 2). In some implementations the generator sequence subsystem 300 takes the target attribute signal 311 as input. The generator sequence subsystem 300 generates sequences of chemical data that include an ingredient sample at each of multiple time steps, e.g., a sequence of ingredients that compose a chemical formulation. Each time step in a given chemical data sequence corresponds to an ingredient in a chemical formulation, and these ingredients may be ordered in descending concentrations over the time steps of a chemical data sequence. In some implementations, the chemical data sample at each time step in the sequence can include a set of characteristic values providing information about the ingredient sample or the sequence as a whole at that particular time step. The set of characteristic values can include, for example, a concentration percentage of an ingredient from the set of ingredients, the function of an ingredient in the chemical product formulation, a mixing stage of an ingredient from the set of ingredients, and/or the like. For example, in some implementations, the chemical data sample at each time step in the sequence can include the concentration of the ingredient sample corresponding to that time step in relation to the whole sequence of chemical data comprised of that time step and all ingredient samples and their respective concentrations at each of the other multiple time steps. As another example, a value included in a chemical data sample at each time step may be the function of an ingredient in the chemical product formulation, e.g., a value corresponding to the function solvent to describe the role of water in a formulation when generating chemical data sequences that compose a skin care product such as a moisturizer.

As shown in FIG. 3, the neural network generator sequence subsystem 300 includes a recurrent subnetwork 310 and one or more output layers 320 (only one of which are labeled in FIG. 3 for simplicity). The recurrent subnetwork 310 and output layers 320 may comprise of one or more signal processing layers. As examples, the recurrent network 310 can include stacked long short-term memory (LSTM) cells and the output layers 320 can be time-distributed dense layers on top of the recurrent network 310. In some implementations, the recurrent subnetwork writes to and reads from an external memory component. In general, the neural network generator sequence subsystem 300 generates the chemical data sequences autoregressively. Thus, for each time step in a chemical data sequence, the neural network generator sequence subsystem 300 generates the chemical data sample at that particular time step given the chemical data samples that have previously been generated in the sequence, i.e., the chemical data samples at all or a subset of the time steps before that particular time step. In some implementations, when the generation has not yet commenced, the first input to the recurrent network 310 at the first time step is configured to begin the generation. In some implementations, the neural network generator sequence subsystem 300 will generate sequences for an arbitrary number of time steps until some stopping condition is reached and the generation ceases. For example, in some implementations, the generation will continue indefinitely (or repeat) until a pre-determined condition is met. The pre-determined condition, in some implementations, can be the neural network of neural network generator sequence subsystem 300 produces a particular chemical data sample that indicates the generation will cease at that particular time step. In some other implementations, the pre-determined condition can be that the generation may be configured to run for a certain number of time steps before ceasing.

At each time step during the generation of a chemical data sequence, the recurrent subnetwork 310 receives as input the current chemical data sequence. In some embodiments, the current chemical data sequence is a chemical data sequence that has been generated partially or wholly by the generator as of that time step. In some implementations, the current chemical sequence may be given as input without having been generated by the recurrent subnetwork 310 previously. The recurrent subnetwork 310 processes the current chemical data sequence and creates an alternative representation of the current chemical sequence at that particular time step. By way of example, FIG. 3 shows the autoregressive generation of a chemical data sequence. To generate a chemical data sample, the recurrent subnetwork 310 receives the current chemical data sequence comprised of the chemical data samples corresponding to time steps before the current time step, and transforms the current chemical data sequence into an alternative representation 312 (only one of which are labeled in FIG. 3 for simplicity).

After the recurrent subnetwork 310 produces the alternative representation 312 at each of the time steps, this alternative representation 312 is received as input by each of the output layers 320 at the corresponding time steps.

In some implementations, the processor at the chemical product formulation apparatus 100 (executing the neural network generator sequence subsystem 300 based on instructions stored in the memory of the chemical product formulation apparatus 100) can be configured to determine, using a neural network and with the chemical data sequence and the set of characteristic values as input, a set of scores of the set of ingredients and associated with the set of target attributes. One output layer generates a score distribution (or a set of scores) over possible ingredient samples for that time step. The score distribution is comprised of respective scores for each of the multitude of possible ingredient samples. In some implementations, one output layer generates a score distribution over possible ingredient functions for that time step where the score distribution is comprised of respective scores for each of the multitude of possible ingredient functions. Here, ingredient "function" is defined as the intended purpose for using the ingredient in the formulation, e.g., water acting as a solvent or propylene glycol acting as a humectant. In some implementations, one output layer generates a score distribution over possible ingredient concentration bins for that time step where the score distribution is comprised of respective scores for each of the multitude of possible ingredient concentration bins, e.g. 0%-1%, 1%-3%, etc. These examples are not meant to be exhaustive, and one can readily implement some other implementations in which one or more output layers generate score distributions over possible sequence attribute categories for that time step where the score distributions are comprised of respective scores for each of the multitude of possible sequence attribute categories. In some implementations, the output layers for generating a score distributions over a multitude of possible choices are softmax output layers. In some implementations, one or more output layers generate numerical values correlated to sequence attributes for that particular time step. By way of example, this can include a numerical value corresponding to the concentration of the ingredient sample at that particular time step. In some implementations, the output layers for generating numerical values are rectified linear layers.

In some implementations, when one or more of the output layers has generated a score distribution corresponding to the multitude of possible samples for that output layer at a particular time step, the generator sequence subsystem 310 selects a sample for each of the output layers at that particular time step in accordance with the score distribution produced by the output layers at that time step. By way of example, the sample selected for a given output layer at a particular time step can be chosen by selecting the sample that has the highest score in the score distribution produced by the given output layer at that time step. As another example, the sample selected for a given output layer at a particular time step can be chosen by sampling the possible samples by weighting each sample's likelihood to be chosen in accordance to its score in the score distribution produced by the given output layer at that time step. The set of all samples and values from all output layers constitutes a complete chemical data sample for that time step. Here, "complete" indicates that the chemical data sample for a particular time step contains all information necessary to generate a chemical data sample at the following time step.

In some implementations, the generator sequence subsystem 310 is configured to take additional neural network input. In some implementations, the neural network input includes one or more local features. Here, local features are features that can differ at each of the multitude of time steps in the chemical data sequence. In some implementations, the neural network input includes one or more global features. Here, global features are features that do not change over the entire chemical data sequence. By way of example, the global feature can be the type of product the generator is configured to produce as an output sequence, e.g., a facial moisturizer v. a facial cleanser in the context of skincare products. In some implementations, where the generator sequence subsystem takes as input a target attribute signal 311, the signal is used as neural network input.

While a generator subsystem with only a single instance of a generator sequence subsystem has been discussed thus far, embodiments are not limited to this arrangement. In some other embodiments a generator subsystem may comprise multiple instances of generator sequence subsystems. In some such embodiments the generators operate in parallel producing one or more chemical data sequences as output. The output of the generator subsystem is taken to be the collections of chemical data sequences produced by all generator sequence subsystems.

Figure 4:
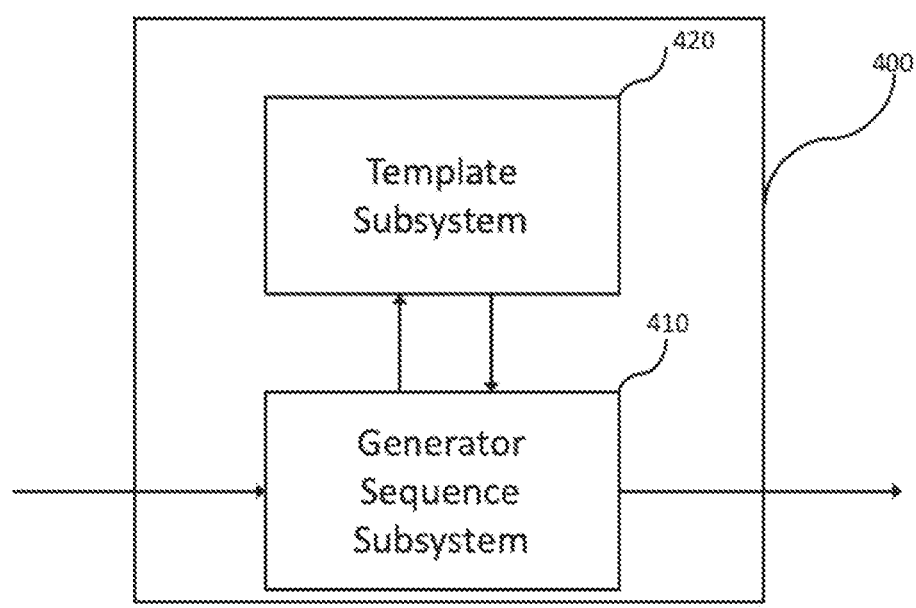
FIG. 4 illustrates a generator subsystem containing one generator sequence subsystem and one template subsystem, according to an embodiment.

FIG. 4 illustrates a generator subsystem 400 having a generator sequence subsystem 410 and a template subsystem 420. The generator subsystem 400 can be stored in a memory and executed by a processor of a chemical product formulation apparatus (similar to the chemical product formulation apparatus 100 in FIG. 1 or the chemical product formulation apparatus 200 in FIG. 2). In general, when the two subsystems are present, the generator sequence subsystem 410 receives input and produces output as described above, but the template subsystem 420 has the ability to modify the chemical data sequences that are input to and/or generated by the subsystem 410 before each time step is generated. In some embodiments, the two subsystems work in series. The current chemical data sequence is communicated to the template subsystem 420, which may make modifications to the sequence, or make no changes, and then the template subsystem 420 outputs a modified current chemical data sequence that is communicated back to the generator sequence subsystem 410.

In some implementations, the template subsystem 420 can provide the generator sequence subsystem 410 a base chemical data sequence of one or more time steps from which the generator sequence subsystem 410 performs autoregressive generation. For example, if the chemical data sequence is comprised of an ingredient and its corresponding concentration at each time step, the template subsystem 420 may provide the generator sequence subsystem 410 with the first two time steps of the chemical data sequence from a source that is not previous output of the generator sequence subsystem 410. In this example, instead of beginning generation from the start signal, the generator sequence subsystem 410 would begin generation at the third time step. In some implementations, the template subsystem 420 may append one or more time steps to the current chemical data sequence. For example, the template subsystem 420 may be configured to insert another time step into the chemical data sequence after a particular time step has been reached. As another example, the template subsystem 420 may be configured to insert another time step into the chemical data sequence after a certain condition in the chemical data sequence has been met, such as a particular ingredient sample being present in the most recently produced time step. Note that the previously-given examples are not the only ways in which the template subsystem 420 can modify the current chemical data sequence, and one will readily appreciate that many such examples are possible.

Figure 5:
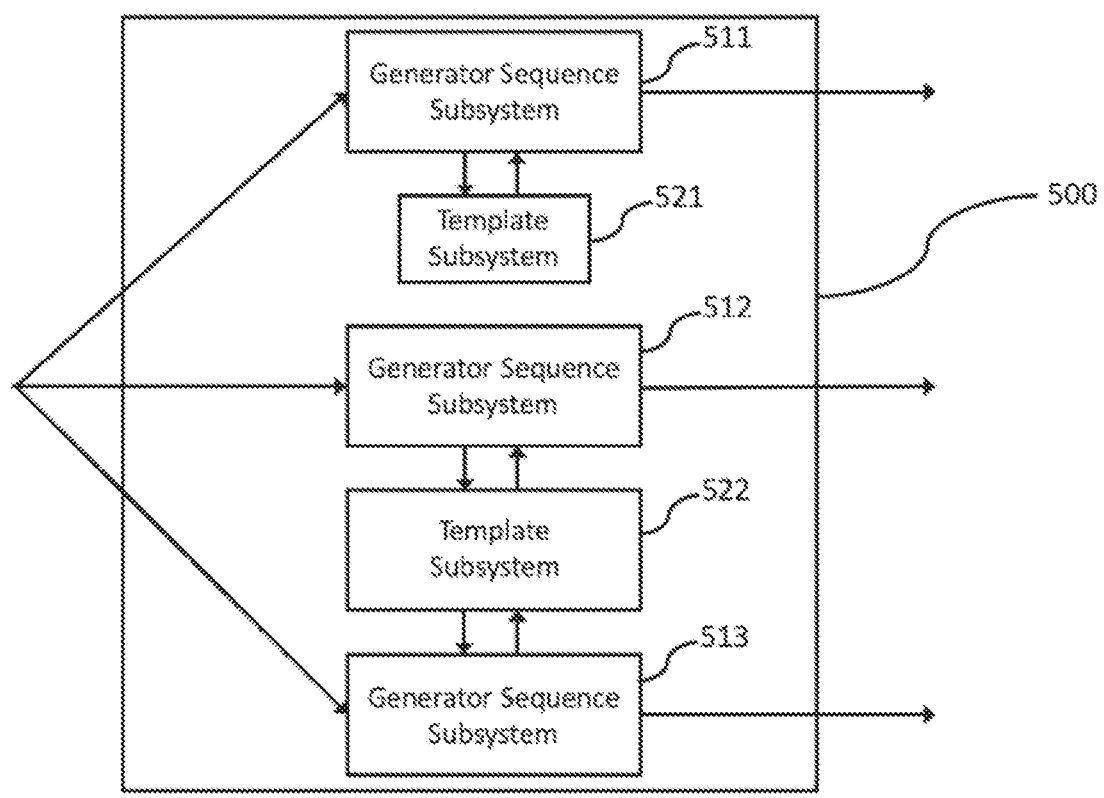
FIG. 5 illustrates a generator subsystem containing three generator sequence subsystems and two template subsystems, according to an embodiment.

Note that FIG. 4 illustrates only one possible embodiment of a generator subsystem containing at least one each of a generator sequence subsystem and a template subsystem. Alternative embodiments of the generator subsystem may comprise multiple instances of generator sequence subsystems and template subsystems. FIG. 5 depicts one possible configuration of a generator subsystem 500 including two template subsystems, 521 and 522, and three generator sequence subsystems, 511-513. The generator subsystem 500 can be executed by the processor of the chemical product formulation apparatus based on instructions stored in a memory of the chemical product formulation apparatus (similar to the chemical product formulation apparatus 100 and 200 described in FIG. 1 and FIG. 2, respectively.) Embodiments of the generator subsystem may be configured with any number of arbitrary topologies of generator sequence subsystems and template subsystems. A single template subsystem may be coupled to one or more generator sequence subsystems.

Returning to FIG. 1, the chemical data sequences generated by the generator subsystem 120 are communicated to and used as input by the predictor subsystem 140. In some embodiments the predictor subsystem 600 includes a recurrent subnetwork 610 and one or more output layers 620. The predictor subsystem 600 can be executed by the processor of the chemical product formulation apparatus based on instructions stored in a memory of the chemical product formulation apparatus (similar to the chemical product formulation apparatus 100 and 200 described in FIG. 1 and FIG. 2, respectively.) The recurrent subnetwork 610 and output layers 620 may comprise of one or more signal processing layers. In general, the predictor subsystem, or predictor, receives as input a chemical data sequence 601, as defined above, and produces as output numerical values and/or classes associated with attributes of the formulation associated with the input chemical data sequence 601. For example, the output can be the final pH value of the product formulated according to a chemical data sequence comprising the ingredient components of a chemical formulation produced by a recurrent subnetwork comprised of LSTM cells.

Figure 6:
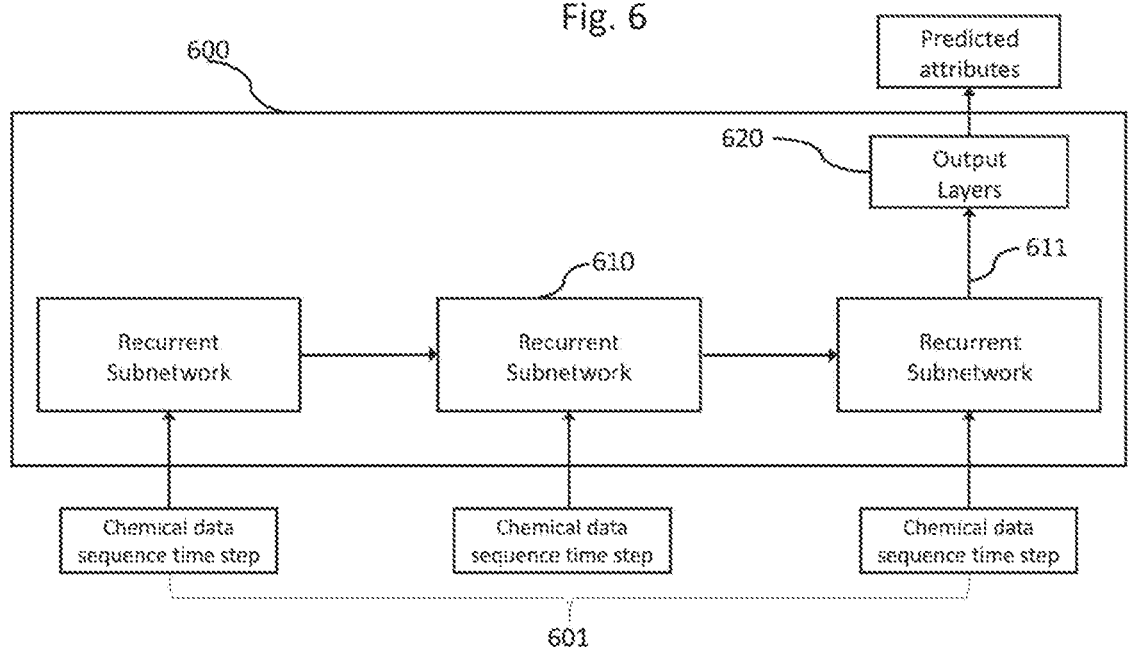
FIG. 6 illustrates a predictor subsystem for predicting attributes of chemical formulation represented by input chemical data sequences, according to an embodiment.

The recurrent subnetwork 610 processes the input chemical data sequence 601 and creates an alternative representation 611 of the current chemical data sequence as a whole. By way of example, FIG. 6 shows the attribute prediction of a product formulated according to an input chemical data sequence 601.

After the recurrent subnetwork 610 produces the alternative representation 611 for the input chemical data sequence 601, this alternative representation 611 is received as input by each of the one or more output layers 620. In some implementations, one or more output layers 620 generates a score distribution over possible attribute categories for the sequence on which the respective output layer weights have been trained. The score distribution is comprised of respective scores for each of the multitude of possible attribute categories for each of the attributes. By way of example, for a predictor subsystem predicting on a chemical data sequence representing the ingredient components of a chemical formulation, a prediction attribute for which an output layer produces a score distribution can be whether any of the component ingredients of the formulation are petrochemically derived. The two possible categories for this attribute are yes and no for if none of the ingredients are petrochemically derived and if one or more of the ingredients are petrochemically derived, respectively. In some implementations, the output layers for generating a score distributions over a multitude of possible choices are softmax output layers.

In some implementations, one or more output layers 620 generates a numerical value correlated to chemical sequence attributes. By way of example, for a predictor subsystem 600 predicting on a product chemical data sequence 601 representing the ingredient components of a chemical formulation, a prediction attribute for which an output layer 620 produces a numerical value can be the pH level of the product as formulated by the chemical data sequence 601. In some implementations, the output layers 620 for generating numerical values are rectified linear layers.

In some implementations, when one or more of the output layers 620 has generated a score distribution corresponding to the multitude of possible attribute categories for that output layer, the predictor subsystem 600 selects an attribute category for each of the output layers 620 in accordance with the score distribution produced by that output layer. By way of example, the sample selected for a given output layer 620 can be chosen by selecting the sample that has the highest score in the score distribution produced by the given output layer. In other words, the processor at the chemical product formulation apparatus can be configured to select, based on the scores and the target attributes, a sample formulation from the set of sample formulations having a score greater than remaining scores from the set of scores. As another example, the sample selected for a given output layer 620 can be chosen by sampling the possible samples by weighting each sample's likelihood to be chosen in accordance to its score in the score distribution produced by the given output layer. In some other implementations, the score distribution produced by one or more output layers 620 may be taken to be the output of that particular layer.

Returning to FIG. 1, the output given by the predictor 140 is communicated to the formulation selector 130. Here, output is taken to be a collection, e.g., a list or set, of the outputs produced by the predictor subsystem 140 for each of the output layers of the predictor subsystem 140.

In some implementations, the chemical data sequences generated by the generator subsystem 120 are communicated to and used as input by a discriminator subsystem 150 (executed by the processor of the chemical product formulation apparatus 100 based on instructions stored in the memory of the of the chemical product formulation apparatus 100). In some implementations, the discriminator subsystem 150 includes a recurrent subnetwork and an output layer (not shown in FIG. 1). The recurrent subnetwork and output layer may comprise of one or more signal processing layers (not shown in FIG. 1). In some implementations, the discriminator subsystem 150 includes a convolutional subnetwork and an output layer (not shown in FIG. 1). The convolutional subnetwork may comprise of one or more signal processing layers, and may use several layers in parallel with different filter sizes. For example, the convolutional subnetwork can be comprised of stacked 1D convolutional layers. In general, the discriminator subsystem 150, or discriminator, receives as input a chemical data sequence, as defined previously, and produces as output a class associated with the origin of a product formulated by a chemical input sequence among a multitude of possible options. In some implementations, the discriminator 150 is configured to determine, using a chemical data sequence as input, an origin associated with the chemical data sequence, and generate a report when the origin is included in a pre-determined group (e.g., having been produced by the chemical product formulation apparatus versus being a member of a set of products currently in the market).

The subnetwork processes the input chemical data sequence and creates an alternative representation of the current chemical data sequence as a whole. After the subnetwork produces the alternative representation for the input chemical data sequence, this alternative representation is received as input by the output layer that generates a score distribution over possible sources of the input chemical data sequence.

In some implementations, the discriminator subsystem 150 selects a source for the input chemical data sequence in accordance with the score distribution produced by the output layer. By way of example, the sample selected for a given output layer can be chosen by selecting the sample that has the highest score in the score distribution produced by the output layer. As another example, the sample selected for the output layer can be chosen by sampling the possible samples by weighting each sample's likelihood to be chosen in accordance to its score in the score distribution produced by the output layer. In some other implementations, the score distribution produced by the output layer may be taken to be the output of discriminator 150.

As shown in FIG. 1, the output given by the discriminator 150 is communicated to the formulation selector 130.

After the generator subsystem 120 has generated chemical data sequences, these chemical data sequences are communicated to the formulation selector 130 in addition to the target attribute signal 111 encoded by the signal encoder 110.

The formulation selector 130 (executed by the processor of the chemical product formulation apparatus 100 based on instructions stored in the memory of the chemical product formulation apparatus 100) is responsible for transforming the input chemical data sequences into viable chemical formulations. In some implementations, all the information related to formulation is encoded in the chemical data sequence. In some other implementations, the chemical data sequence contains some portion of the information related to formulation and the formula selector 130 provides any remaining information during the transformation process. For example, a chemical data sequence may include an ingredient sample and its corresponding concentration at each time step. If the ingredient concentrations do not sum up to 100%, the formulation selector may scale the values so that they do sum to 100%. The formulation then would include a list of ingredients found in the chemical data sequence and their corresponding scaled concentration value.

The formulation selector 130 is responsible for selecting a subset of the chemical formulations corresponding to their respective input chemical data sequences to be taken as the output of the formulation selector. The formulation selector 130 may make the selection of a particular formulation or particular formulations so as to achieve a wide variety of objectives. In some implementations, this selection is informed by the target attribute signal 111. Stated similarly, the formulation selector 130 can be configured to select, based on the score distribution and the target attributes, a sample formulation from the set of sample formulations having a score greater than remaining scores from the score distribution. The subset can range from the empty set to the full set of transformed chemical data sequences. There are many possible methods by which the formulation selector 130 may determine the subset of transformed chemical formulations that will be output for any configuration of the formulation selector 130. For example, in a configuration where the apparatus contains no predictor and no discriminator, the formulation selector may simply select an arbitrary number of randomly-selected transformed chemical formulations.

In some implementations, the formulation selector may also receive as input predicted attribute values corresponding to each chemical data sequence if the chemical product formulation apparatus 100 is configured to include a predictor subsystem 140. In some implementations, the formulation selector 130 may also receive as input the output of the discriminator subsystem 150 corresponding to each chemical data sequence if the chemical product formulation apparatus 100 is configured to include a discriminator subsystem 150. In some implementations, the transformed chemical formulations are selected to best optimize matching the target attribute signal 111 to the predictor 140 and/or discriminator 150 output values corresponding to those found in the target attribute signal 111. For example, if the target attribute signal 111 comprises a signal encoding a desired pH of 5, then formulations may be selected so that the predicted attribute value corresponding to formulation pH value associated with those formulations are closest to a pH of 5. In other words, the processor at the chemical product formulation apparatus can be configured to select, based on the set of scores and the set of target attributes, a sample formulation from the set of sample formulations having a score greater than remaining scores from the set of scores;

When an attribute is a numerical value, it is desirable to formulate a product for which the attribute value is as close as possible to the target value. For example, for an embodiment with one target attribute, such as a product with a pH value of 5, then an output product with a pH of 5.1 is considered more desirable than an output product with a pH value of 6. When an attribute is a categorical or classification value, it is desirable to formulate a product that belongs to the target category or class, or else a class that is similar to the target category or class. In some instances, there may be multiple of the aforementioned target attributes for which the formulation selector 130 optimizes. In some implementations, the target attributes may be ranked in order of importance for optimization. In this case, optimizing may be done in the order of the target attribute ranking (or priority values of the target attributes), i.e., formulations are optimized on the highest-ranking target attribute and then optimized on the second highest ranking attribute and so on. For example, an implementation configured to optimize in such a manner over two target attributes, one categorical and one numerical, may first select formulations only belonging to a certain category of product and then over this subset optimize and select for formulations nearest the target numerical attribute value. In some implementations, each target attribute may be given a weight and the selected formulations are determined using weighted combinations of the two or more target attributes. For example, an implementation configured in such a manner may use weighted combinations to balance product efficacy and cost of formulation. Embodiments are not limited to these arrangements; in other embodiments the formulation selector 130 may use other methods to perform the optimization and selection over one or more target attributes.

The selected subset of transformed chemical formulations are taken to be the output of the formulation selector 130. While FIG. 1 illustrates a chemical product formulation apparatus 100 with only a single instance of a formulation selector 130, embodiments are not limited to this arrangement. In some other embodiments, a chemical product formulation apparatus may comprise multiple instances of formulation selectors. In some such embodiments, the formulation selectors operate in parallel producing one or more chemical formulations as output. The output of the chemical product formulation apparatus is taken to be the collections of chemical formulations produced by all formulation selector subsystems. In some implementations, the processor at the chemical product formulation apparatus is configured to generate a report (or an output) having information associated with the selected subset of transformed chemical formulations that are associated with the target attributes.

In some embodiments, the processor at the chemical product formulation apparatus can repeat executing the one or more steps described in FIG. 1-FIG. 6 until a pre-determined condition is met. The processor can be configured to repeat by determining a new set of sample formulations and selecting a new sample formulation from the new set of sample formulations. The pre-determined condition, in some implementations, can be the instance of the neural network producing a particular chemical data sample that indicates the generation can cease at that particular time step. The pre-determined condition, in some implementations, can be the generation of a chemical data sample with a particular target attribute. The pre-determined condition, in some implementations, can be the expiration of a pre-determined period of time.

Figure 7:
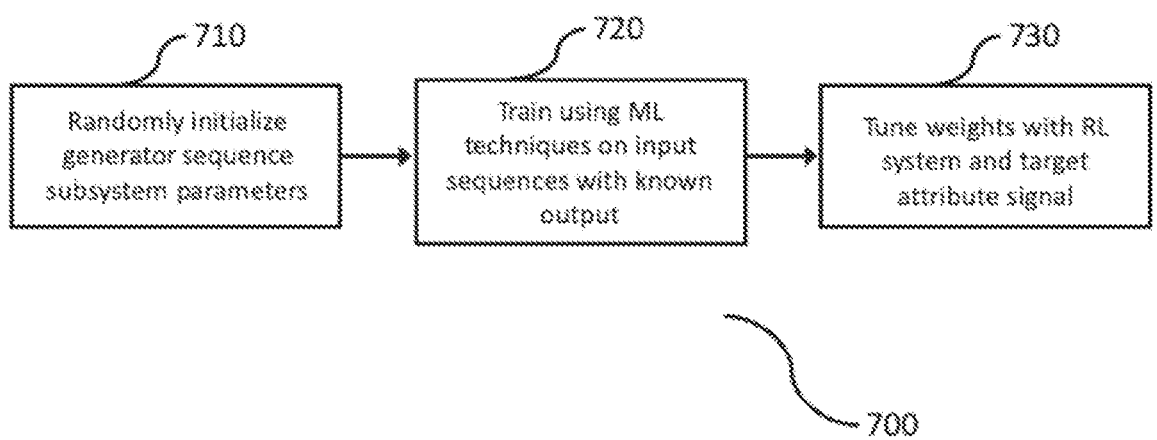
FIG. 7 illustrates a method for the conditioning of the generator sequence subsystem to produce chemical data sequences more likely to represent formulations exhibiting desired attributes, according to an embodiment.

In addition to using the target attribute signal 111 to condition the generator subsystem 120 to produce chemical data sequences that should transform into chemical formulations with the desired target attributes, the neural network generator sequence subsystem can also be trained before the apparatus is used so that the neural network generator sequence subsystem tends to produce chemical data sequences that are more likely to accomplish the aforementioned objective. FIG. 7 illustrates the method 700 of training the neural network generator sequence subsystem, for one embodiment of the subsystem. The method 700 can be executed by a processor of a chemical product formulation apparatus according to instructions stored in a memory of the chemical product formulation apparatus (similar to the chemical product formulation apparatus 100 in FIG. 1 or the chemical product formulation apparatus 200 in FIG. 2).

The neural network generator sequence subsystem parameters may be randomly initialized, 710. In some embodiments, the neural network generator sequence subsystem may be trained on all layers with parameters using known machine learning training techniques, e.g., stochastic gradient descent with backpropagation, on a set of inputs for which the chemical data sequence that should be generated by the subsystem is known, 720. For example, the inputs can be chemical data sequences representing existing chemical products that have been previously formulated and are known to be chemically stable. In this case, at any point in the sequence, the next output at any particular time step that should be generated is the next time step in the input sequence.

The neural network generator sequence subsystem can be further trained using a target attribute signal, in 730, so that the formulations corresponding to chemical data sequences generated by the subsystem are more likely to exhibit the desired attributes communicated through the target attribute signal. In some implementations, this is achieved through the use of a reinforcement learning subsystem termed the tuning subsystem or tuner (not shown). The tuner is configured to receive as input a target attribute signal and the generator sequence subsystem as well as one or more of the following: the output of the predictor subsystem if present, the output of the discriminator subsystem if present. The tuner is configured to modify the neural network weights of the neural network generator sequence subsystem with the aim of modifying the output of the neural network generator sequence subsystem (or to increase the scores of the ingredients) so that the formulations represented by the output chemical data sequences exhibit the desired attributes encoded in the target attribute signal. In some implementations, the tuner (or the processor at the chemical product formulation apparatus executing the tuner based on instructions stored in the memory of the chemical product formulation apparatus) modifies the neural network weights to generate a modified neural network. The processor at the chemical product formulation apparatus can determine, based on the modified neural network, a modified chemical data sequence including a modified plurality of ingredients. In some implementations, the tuner can modify the neural network weights based on priority values associated with the target attributes. For example, if the pH level of the chemical product formulation has a higher priority than the viscosity of the chemical product formulation, the tuner can modify the neural network weights to achieve the desired pH level. The tuning subsystem may be trained using known reinforcement learning techniques, e.g., by using a policy gradient method.

Figure 8:
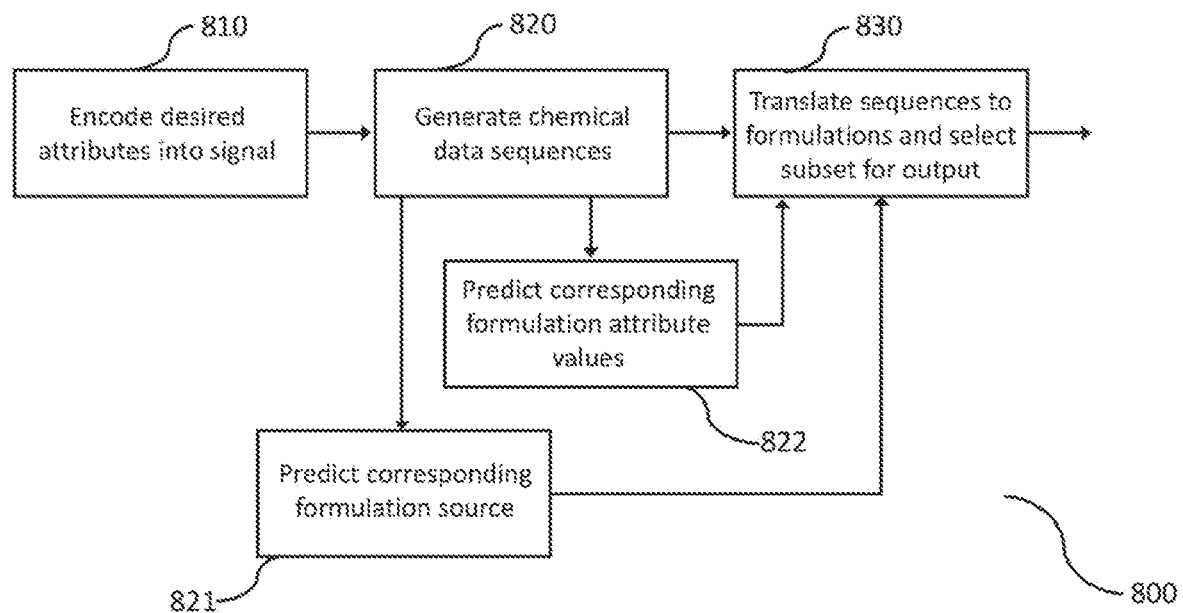
FIG. 8 illustrates a method for the chemical formulation of products with desired formulation attributes, according to an embodiment.

FIG. 8 illustrates a method 800 for the chemical formulation of products with desired formulation attributes. The method 800 can be executed by a processor of a chemical product formulation apparatus according to instructions stored in a memory of the chemical product formulation apparatus (similar to the chemical product formulation apparatus 100 in FIG. 1 or the chemical product formulation apparatus 200 in FIG. 2). The method begins with 810, encoding a target attribute signal from an input of desired attributes. Next, one or more chemical data sequences are generated in 820. The attributes of formulations represented by the chemical data sequences are predicted at 821. The source of the formulations represented by the chemical data sequences are predicted at 822. The generated chemical data sequences are then translated to chemical formulations and a subset of the formulations are selected as output with 830. The formulations selected for output are determined by the target signal and their corresponding predicted attributes and predicted source if optional 821 and 822 are present, respectively.

Implementations, subject matter, and operational functions described herein can be constructed in digital electronic circuitry, in tangible computer software or firmware, in computer hardware, including the structures discussed in this description and their structural equivalents, or in combinations of multiple embodiments.

Implementations of the invention, subject matter, and operational functions described herein can be constructed as one or multiple computer programs. The term "computer program" is used to describe one or more modules of computer program instructions encoded on a tangible, non-transitory program carrier for execution by, or to control the operation of, data processing apparatus. These program instructions can be encoded on a digitally propagated signal such as a machine-generated electrical, optical, or electromagnetic signal. These signals are generated to encode the program instructional information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses a variety of different apparatus, devices, and machines for processing data, including programmable processors, computers, or a combination of these. The apparatus can include special purpose logic circuitry, such as an FPGA (field programmable gate array) or an ASIC (application specific integrated circuit). The apparatus can also include, but is not limited to, code that creates an environment for the execution of the computer program in question, such as code that constitutes processor firmware, a protocol stack, a database management system, an operating system, or a combination of these.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random-access memory or both. A computer can include a central processing unit for performing or executing instructions and one or more memory devices for storing instructions and data. Generally, a computer can also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosure or of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular implementations, subject matter, and its operational functions have been described. Also, the processes depicted in the accompanying schematic figures do not necessarily require the particular order shown, or sequential order, to achieve desirable results. Within the context of certain implementations, multitasking and parallel processing may be advantageous.

What is claimed is:

1. A method, comprising:
receiving a plurality of target attributes associated with a chemical product formulation and a plurality of priority values of the plurality of target attributes;
determining, based on (1) a first neural network, (2) the plurality of target attributes and (3) the plurality of priority values, a plurality of sample formulations, each sample formulation from the plurality of sample formulations including a plurality of ingredients;
determining a plurality of scores based on the plurality of sample formulations, each score from the plurality of scores being associated with a sample formulation from the plurality of sample formulations;
selecting, based on the plurality of scores and the plurality of target attributes, a sample formulation from the plurality of sample formulations having a score greater than remaining scores from the plurality of scores;
determining an origin associated with the sample formulation; and
when the origin is included in a pre-determined group, generating a report including the sample formulation as the chemical product formulation.

2. The method of claim 1, wherein:
the plurality of sample formulations is a first plurality of sample formulations;
the sample formulation is a first sample formulation;

the method further includes:
modifying a plurality of weights associated with the first neural network to determine a second plurality of sample formulations;
selecting a second sample formulation from the second plurality of sample formulations; and
the report includes the second sample formulation as the chemical product formulation.

3. The method of claim 1, wherein:
the plurality of sample formulations is a first plurality of sample formulations;
the sample formulation is a first sample formulation;
the method further includes:
modifying the first sample formulation to generate a modified sample formulation;
determining, based on the first neural network and the modified sample formulation, a second plurality of sample formulations; and
the report includes a second sample formulation selected from the second plurality of sample formulations as the chemical product formulation.

4. The method of claim 1, further comprising:
repeating until a pre-determined condition is met:
determining a new plurality of sample formulations; and
selecting a new sample formulation from the new plurality of sample formulations.

5. The method of claim 1, wherein:
the plurality of target attributes includes at least one of a class, a viscosity, or a pH level.

6. The method of claim 1, wherein:
the first neural network includes a recurrent subnetwork.

7. The method of claim 1, wherein:
the chemical product formulation is a skin care product.

8. A non-transitory processor-readable medium storing code representing instructions to be executed by a processor, the code comprising code to cause the processor to:
receive a plurality of target attributes for a chemical formulation;
encode the plurality of target attributes to generate a signal;
determine, using a first neural network with the signal as a first input, (1) a chemical data sequence including a plurality of ingredients and (2) a plurality of characteristic values, each ingredient from the plurality of ingredients associated with a characteristic value from the plurality of characteristic values;
determine, using a second neural network and with the chemical data sequence and the plurality of characteristic values as a second input, a plurality of scores of the plurality of ingredients and associated with the plurality of target attributes;
modify a plurality of weights associated with the first neural network to increase the plurality of scores and generate a modified neural network;
determine, based on the modified neural network, a modified chemical data sequence including a modified plurality of ingredients; and
generate a report including the chemical formulation having the modified chemical data sequence associated with the plurality of target attributes.

9. The non-transitory processor-readable medium of claim 8, wherein the chemical formulation is a personal care product formulation.

10. The non-transitory processor-readable medium of claim 8, wherein the code to cause the processor to generate the report further includes code to cause the processor to:
determine, using the modified chemical data sequence as a third input, an origin associated with the modified chemical data sequence; and
generate the report when the origin is included in a pre-determined group.

11. The non-transitory processor-readable medium of claim 8, wherein:
each characteristic value from the plurality of characteristic values is associated with a concentration percentage of an ingredient from the plurality of ingredients and from a plurality of concentration percentages.

12. The non-transitory processor-readable medium of claim 8, wherein:
each characteristic value from the plurality of characteristic values is associated with a mixing stage of an ingredient from the plurality of ingredients and from a plurality of mixing stages.

13. The non-transitory processor-readable medium of claim 8, wherein:
the plurality of target attributes includes at least one of a class, a viscosity, or a pH level.

14. The non-transitory processor-readable medium of claim 8, wherein the code to encode the plurality of target attributes to generate a signal includes code to cause the processor to perform one-hot encoding.

15. The non-transitory processor-readable medium of claim 8, wherein the code to encode the plurality of target attributes to generate the signal includes code to cause the processor to map the plurality of target attributes to a pre-determined set of discrete values when the plurality of target attributes is continuous.

16. The non-transitory processor-readable medium of claim 8, wherein:
the first neural network includes a recurrent subnetwork and one or more output layers,
the recurrent subnetwork includes stacked long short-term memory cells, and
the one or more output layers includes time-distributed dense layers.

17. The non-transitory processor-readable medium of claim 8, wherein the code further includes code to cause the processor to:
receive a base chemical data sequence,
the code to determine the chemical data sequence includes the code to cause the processor to determine the chemical data sequence based on the base chemical data sequence.

18. The non-transitory processor-readable medium of claim 8, wherein:
each target attribute from the plurality of target attributes is associated with a priority value from a plurality of priority values,
the code to cause the processor to modify the plurality of weights associated with the first neural network is based on the plurality of priority values.

19. The non-transitory processor-readable medium of claim 8, wherein the code further includes code to cause the processor to train the first neural network using a stochastic gradient descent with backpropagation technique based on a training data set.

20. The non-transitory processor-readable medium of claim 8, wherein the code to cause the processor to modify the plurality of weights further includes code to cause the processor to:
modify the plurality of weights using reinforcement learning.

21. The non-transitory processor-readable medium of claim 8, wherein the code further includes code to cause the processor to:
repeat determining a new chemical data sequence until a pre-determined condition is met.

22. An apparatus, comprising:
a processor; and
a memory operatively coupled to the processor, the memory storing code representing instructions to be executed by a processor, the code comprising code to cause the processor to:
receive a plurality of target attributes associated with a chemical product formulation;
determine, based on a first neural network, a first plurality of sample formulations associated with the plurality of target attributes, each sample formulation from the first plurality of sample formulations including a plurality of ingredients;
determine a first plurality of scores, each score from the first plurality of scores associated with a sample formulation from the first plurality of sample formulations;
select, based on the first plurality of scores and the plurality of target attributes, a first sample formulation from the first plurality of sample formulations having a score greater than remaining scores from the first plurality of scores;
determine, based on the first neural network and the first sample formulation, a second plurality of sample formulations;
determine a second plurality of scores, each score from the second plurality of scores associated with a sample formulation from the second plurality of sample formulations;
select, based on the second plurality of scores and the plurality of target attributes, a second sample formulation from the second plurality of sample formulations having a score greater than remaining scores from the second plurality of scores;
determine an origin associated with the second sample formulation; and
when the origin is included in a pre-determined group, generate a report including the second sample formulation as the chemical product formulation.

23. The apparatus of claim 22, wherein the code further includes code to cause the processor to:
repeat until a pre-determined condition is met:
determining a new plurality of sample formulations; and
selecting a new sample formulation from the new plurality of sample formulations.

* * * * *